United States Patent [19]

Mo

[11] Patent Number: 5,597,550
[45] Date of Patent: Jan. 28, 1997

[54] APPARATUS AND METHOD FOR ADMINISTERING MINERALS

[76] Inventor: Buxing Mo, 1060 Kam Hwy. #303A, Pearl City, Hi. 96782

[21] Appl. No.: 354,209

[22] Filed: Dec. 9, 1994

[51] Int. Cl.$^6$ .................................................. A61K 33/00
[52] U.S. Cl. .............................. 424/40; 424/41; 424/600; 424/601; 424/620; 424/630; 424/639; 424/641; 424/642; 424/646; 424/650; 424/655; 424/661; 424/667; 424/682; 424/702; 424/703; 424/653
[58] Field of Search .................... 424/40, 41, 600, 424/601, 620, 630, 639, 641, 642, 646, 650, 655, 661, 667, 682, 702, 703, 653

[56] References Cited

U.S. PATENT DOCUMENTS

| | | |
|---|---|---|
| 536,707 | 4/1895 | Smith . |
| 762,256 | 6/1904 | Schneider ................................. 424/41 |
| 763,765 | 6/1904 | Johnson . |
| 2,539,036 | 1/1951 | Schwab . |
| 3,620,453 | 11/1971 | Grancberg ................................ 424/41 |
| 3,744,491 | 7/1973 | Fischer . |
| 4,199,548 | 4/1980 | Kaiho et al. . |
| 4,285,905 | 8/1981 | Feit . |
| 4,328,319 | 5/1982 | Osipow et al. . |
| 4,340,053 | 7/1982 | Sarui ........................................ 424/40 |
| 4,706,676 | 11/1987 | Peck . |
| 4,747,841 | 5/1988 | Kuratomi et al. . |
| 4,758,425 | 7/1988 | Denick, Jr. et al. . |
| 4,895,727 | 1/1990 | Allen . |
| 5,029,579 | 7/1991 | Trammell . |
| 5,204,119 | 4/1993 | Shiobara et al. . |
| 5,487,883 | 1/1996 | Yoo ........................................... 424/40 |

OTHER PUBLICATIONS

The Wellness Encyclopedia by University of California, Berkeley pp. 114–116.

*Primary Examiner*—Amy Hulina
*Attorney, Agent, or Firm*—Martin E. Hsia

[57] ABSTRACT

An apparatus and process for administering minerals to the human body by mixing pre-selected particulated minerals with graphite and coal tar to form a bar (10a), vaporizing the bar (10a) to form a mineral rich vapor, and directing the vapor to a patient's skin using an enclosure (30).

10 Claims, 2 Drawing Sheets

APPARATUS AND METHOD FOR ADMINISTERING MINERALS

TECHNICAL FIELD

This invention relates to an apparatus and method for administering minerals to the human body.

It is well known that the human body needs certain essential chemical elements or compounds (hereinafter collectively referred to as "minerals") in order to stay healthy, often in only trace amounts. Among such minerals are: potassium (K), sodium (Na), calcium (Ca), iron (Fe), magnesium (Mg), phosphorus (P), zinc (Zn) and copper (Cu). Traditionally, some of these minerals are provided by injection or ingestion (taken orally as mineral supplements or in fruits, vegetables, meats, and other forms of foods). However, some minerals can be harmful if taken orally or injected directly into the body or if given in excessive amounts. Therefore, there is a need for an effective procedure to administer the trace amounts of these minerals necessary for good health, without undesirable and harmful side effects, such as those caused by overdoses.

Modern western medicine is starting to recognize that shortages of minerals can cause many ailments, and that these ailments can be treated by providing the missing minerals. For example, a shortage of iodine is considered to be the cause of goiter and other thyroid disturbances and is treatable by administering iodine, such as in iodized salt. Presently, twenty two minerals are identified as essential to the body. See *The Wellness Encyclopedia*, University of California, Berkeley, pp. 114–116.

BACKGROUND ART

U.S. Pat. No. 4,747,841 to Kuratomi, et al., discloses methods and apparatus for moxibustion (burning herbs on the skin to treat ailments) in which a heat generating pyrogen heats and vaporizes an herbal material that is adjacent to the skin so that the herbal vapor is absorbed through the skin. The pyrogen contains carbon and various chemicals, but the pyrogen is separated from the herbal material by a non permeable material so that only vapors from the herbal material come into contact with the skin.

U.S. Pat. No. 5,016,652 to Rose, et al., discloses a patch adapted for transdermal administration of nicotine into the bloodstream of a patient.

U.S. Pat. No. 4,328,319 to Osipow, et al., discloses a process for preparing a propellant for forming foamed structures which uses various materials including certain minerals, the foamed structures being usable to apply medicaments to the skin.

U.S. Pat. No. 536,707 to Smith discloses a depurator that drives steam through a medicated material and then into a cabinet into which a patient is placed.

U.S. Pat. No. 763,765 to Johnson discloses a cabinet in which fumes arising from medicaments are contained and directed to parts of the body to be treated.

U.S. Pat. No. 2,539,036 to Schwab discloses a device for holding cartridges of chemical or mineral media in contact with a patient's skin.

U.S. Pat. No. 3,744,491 to Fischer discloses a portable chamber that permits the localized treatment, with low pressure oxygen, of non-healing ulcerations or lacerations.

U.S. Pat. No. 5,029,579 to Trammell discloses a hyperbaric oxygenation apparatus with cyclically variable oxygen pressure.

U.S. Pat. No. 4,199,548 to Kaiho, et al., discloses thermally diffusible composites of medicines, including insecticides, attractants, expellents, rodenticides, cockroachicides and fungicides, using carbonaceous materials and alkali metal compounds.

U.S. Pat. No. 4,285,905 to Feit discloses a method and apparatus for dispersing a volatilizable compound in an environment, especially a heat-stable volatile fragrance.

U.S. Pat. No. 4,706,676 to Peck discloses a sweat collecting device for monitoring chemical exposures.

U.S. Pat. No. 4,758,425 to Denick, Jr., et al., discloses a medicament adsorbate for masking the taste of bitter drug principles.

U.S. Pat. No. 4,895,727 to Allen discloses a method to increase the ability of skin to absorb topically applied pharmacologically active agents while reducing the speed with which the agent is absorbed into the body.

U.S. Pat. No. 5,204,119 to Shiobara, et al., discloses an external preparation capable of controlling the release rate and percutaneous absorbability of a drug.

DISCLOSURE OF INVENTION

The present invention is a process for administering essential minerals to the human body, comprising:

mixing particulated pre-selected minerals with graphite and a petrochemical binder to form a bar;

vaporizing the bar to produce a heated mineral rich vapor; and directing the vapor to the part of the human body to be treated.

Preferably, the vapor is also directed first to the back, from the shoulders to the base of the spine, for fifteen minutes, then on the soles of the feet for another fifteen minutes.

The minerals in the vapor will be absorbed by the patient's skin and into the patient's bloodstream, a process called transdermal absorption or percutaneous absorption.

Preferably the vaporizing step is performed using electricity, but can be performed by using direct or indirect heat at a high enough temperature. Preferably about 90% by weight of the bar is graphite, about 2% by weight of the bar is a petrochemical binder, and the remainder of the bar is the minerals in various proportions that have been preselected depending on the needs of the particular individual. The graphite will contain some trace impurities of beneficial minerals, and the following minerals are preferably added: zinc (Zn), chromium (Cr), magnesium (Mg), sulfur (S) and selenium (Se).

The shape of the bar may vary according to the method used for vaporization or for other reasons. The method of vaporization is not critical. For example, the vaporizing step can be performed by heating with a flame, baking in an oven, or some other method of heating, preferably by passing an electric current through the junction of two bars.

If the vaporization is accomplished by passing an electric current through the junction of two bars, the graphite mixture is preferably formed into cylindrical shapes about six inches (about 18 centimeters) long and about ¼ of an inch (about half a centimeter) in diameter, thus defining an electrode end and a free end of each bar.

To facilitate absorption of the vapor through the skin, a blanket or other covering is placed over the user and the apparatus vaporizing the bar so that the body's own heat and the heat from the vapor heats the skin and opens up the pores. Some of the minerals from the vapor are absorbed into the body through the pores, producing beneficial effects. It is almost impossible to administer an overdose of the minerals because skin absorptivity limits the rate of absorption to safe levels, and even if excess minerals are absorbed through the skin, the body can excrete the excess.

BEST MODE FOR CARRYING OUT INVENTION

The best mode presently contemplated for practicing the subject invention is to mix preselected powdered minerals with graphite and a petrochemical binder, preferably coal tar, to create a graphite/mineral mixture. Preferably the minerals are selected according to the particular ailment to be treated and the needs of the individual patient. Preferably, only enough petrochemical binder is added to bind the graphite and minerals together.

The percentage by weight graphite in the bar is between approximately 70% and approximately 95%, preferably between approximately 85% and 95%, and optimally approximately 89%.

The percentage by weight petrochemical binder in the bar is between approximately 1% and approximately 4%, preferably between approximately 2% and approximately 3%, and optimally approximately 2%.

The percentage by weight minerals in the bar is between approximately 5% and approximately 20%, preferably between approximately 10% and approximately 15%, and optimally approximately 10%.

Among the minerals that can be used in the practice of the invention are the following: calcium (Ca), phosphorus (P), chlorine (Cl), magnesium (Mg), sulfur (S), iron (Fe), copper (Cu), zinc (Zn), chromium (Cr), cobalt (Co), manganese (Mn), molybdenum (Mb), vanadium (Vn), selenium (Se), nickel (Ni), tin (Sn), silicon (Si), iodine (I), arsenic (As), aluminum (Al), titanium (Ti), bismuth (Bi), barium (Ba), strontium (Sr), and germanium (Ge). For example, for treating diabetes, prostate problems and hypertension, it is preferred that the following minerals be used, with the first five listed each comprising more than 1% by weight of the bar: sulfur (S), zinc (Zn), chromium (Cr), magnesium (Mg), selenium (Se), aluminum (Al), iron (Fe), copper (Cu), cobalt (Co), manganese (Mn), tin (Sn), nickel (Ni), silicon (Si), arsenic (As), strontium (Sr), barium (Ba), bismuth (Bi), and titanium (Ti). Because many of these minerals are naturally present in the graphite, it actually may only be necessary to add sufficient amounts of the following minerals to obtain the following percentages by weight of the bar: zinc (Zn): approximately 1% to approximately 3%; chromium (Cr): approximately 1% to approximately 3%; magnesium (Mg): approximately 2% to approximately 5%; sulfur (S): approximately 1% to approximately 2%; and selenium (Se): approximately 1% to approximately 3%. Preferably the minerals are obtained in powdered form and then mixed together with powdered graphite and a petrochemical binder, preferably coal tar, to form a graphite/mineral mixture.

Figure 1:
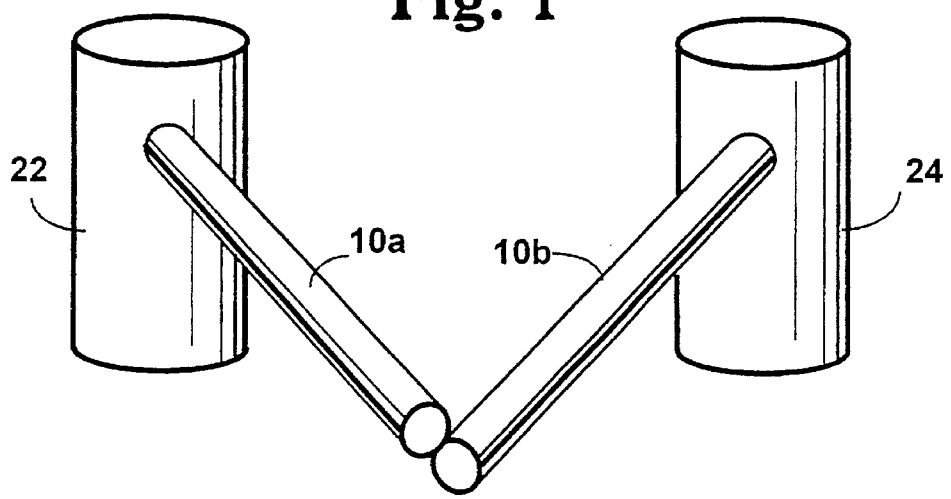
FIG. 1 is a front perspective view of the presently preferred embodiment of two graphite bars according to the present invention attached to electrodes and in contact with each other.

Referring to FIG. 1, the mixture of graphite and minerals is preferably formed into small, preferably cylindrical, bars 10a and 10b, each about the size of a pencil, approximately 5/16" in diameter and approximately 7" in length, each bar having an electrode end and a free end. The bars 10a 10b can be of different lengths, although it is preferable that the combined length of the bars be approximately 14 inches. The electrical resistance of each bar is preferably approximately 0.2 ohm and the weight of each bar is preferably approximately 15 grams. The bars 10a and 10b are preferably vaporized using electricity, preferably by connecting the electrode ends of two bars to electrodes 22, 24 and positioning the bars horizontally, at slightly different heights, so that the bars touch each other at an angle at the free ends, one on top of the other, and complete the electric circuit. Preferably alternating current electricity is then applied to the electrodes at between 12 volts and 25 volts (a safe range for humans to handle) so that a current of between approximately 5 amperes and approximately 10 amperes (preferably approximately 7 amperes) passes through the bars. A current of approximately 5 amperes is necessary in order to cause the bars 10a 10b to vaporize, and a current of greater than approximately 10 amperes makes the bars too hot. Although the resistance of each bar is approximately 0.2 ohms and the total resistance of the two bars is therefore, theoretically, 0.4 ohms, the effective resistance of the two bars when in contact is between approximately 1 and approximately 3 ohms when two completely new bars are touching each other because the area of contact is very small. The resistance of the bars will decrease as the bars become shorter as they are vaporized. The resistance at the point of contact between the bars decreases as the area of contact increases and the resistance increases as ashes from vaporization form, thereby making it necessary to remove the ashes from time to time. The electric current passing through the bars 10 preferably creates sufficient heat at the point of contact of the bars to cause combustion there, causing the graphite, binder and minerals to vaporize. The continuous passing of the electric current maintains combustion at the ends of the graphite bars, thus producing a continuous supply of mineral rich vapor. Preferably the electricity is applied for periods of approximately 15 minutes, although the time is not critical. As the bars 10a, 10b vaporize, they will become shorter, and therefore it is preferred to adjust the positions of the bars 10a, 10b and remove the ashes formed, to maintain contact between their free ends, either manually or by other means, such as spring loaded holders. It is also preferably to provide some mechanism that removes ashes, such as by continuously rotating one or both bars against each other, or otherwise.

Figure 2:
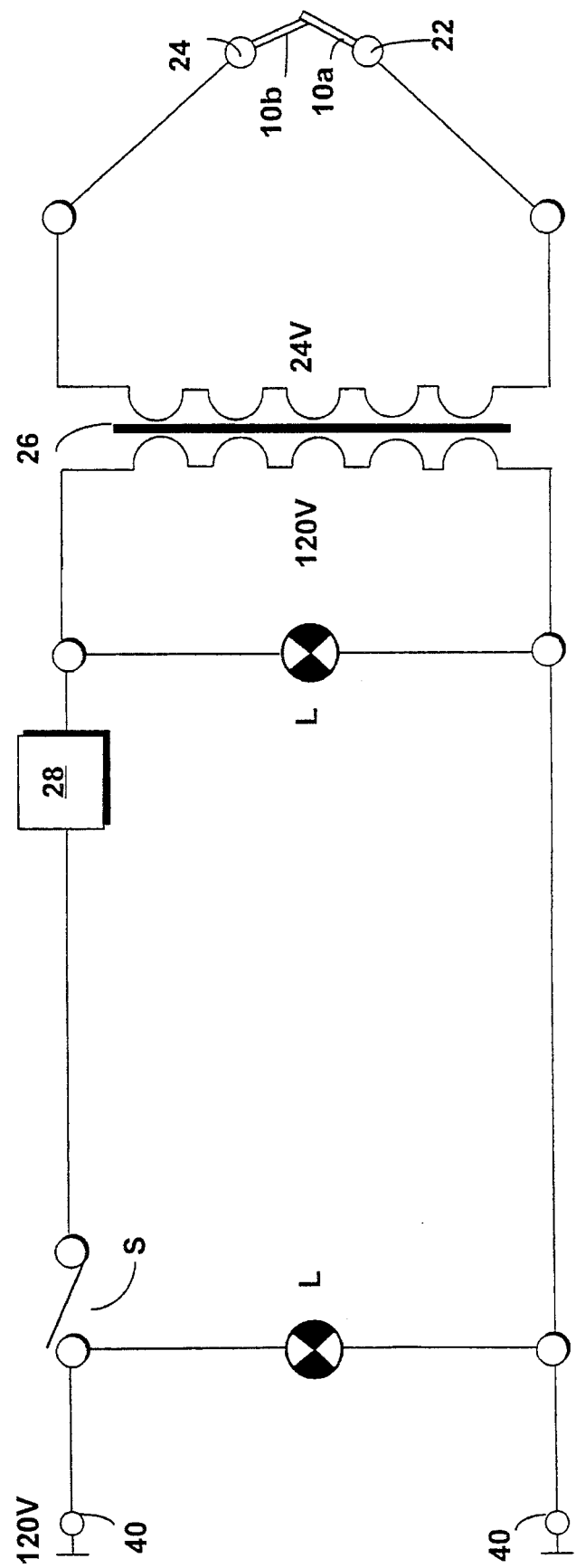
FIG. 2 is a schematic of a presently preferred embodiment of an electrical circuit according to the present invention.

Referring to FIG. 2, shown is a schematic diagram of a presently preferred electric circuit to be used in connection with the present invention. Electrical power (preferably 12 volt alternating current in the United States and the commonly available electric current in other countries) is stepped down to 24 volts using a transformer 26, preferably an iron core transformer. Preferably a timer 28 is provided. Optionally, indicator lights L and a switch S are also provided. When the free ends of the bars 10a and 10b are brought into contact with each other, the electric circuit is completed and the electric current passing through the bars 10a, 10b creates sufficient heat to ignite the bars 10a, 10b and keep them burning at their point of contact, thereby causing the bars 10a, 10b to vaporize and create a heated mineral-rich vapor. The particular point of contact is not critical, but contact at the ends is preferable.

Figure 3:
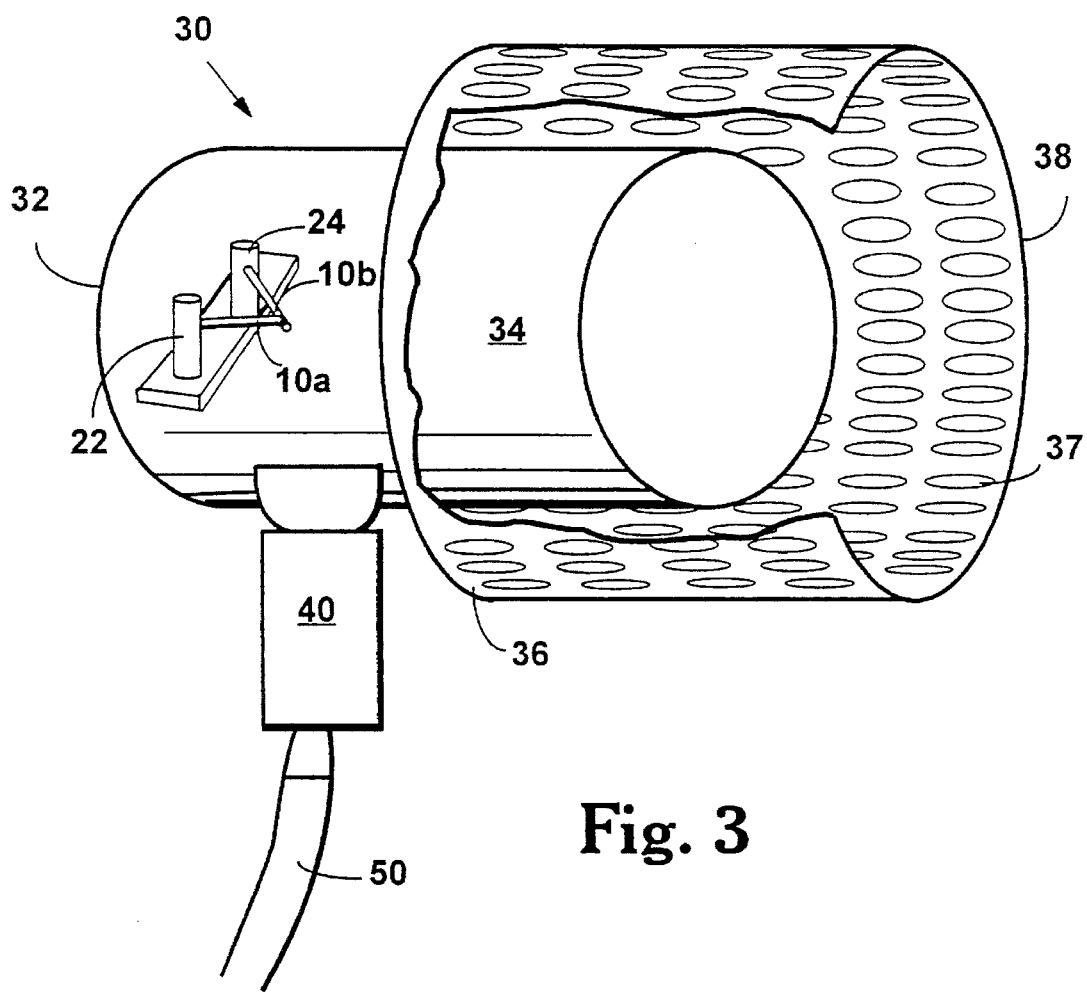
FIG. 3 is a perspective cut away view of a presently preferred embodiment of a vaporizing apparatus according to the present invention.

Preferably, the heated mineral-rich vapor is generated within an enclosure 30 as shown in FIG. 3. Preferably the enclosure 30 comprises an inner cylinder 34 approximately half a meter long and approximately 30 centimeters in diameter, preferably of metal. Preferably an outer cylinder 36 having multiple perforations 37 is coaxially mounted on the inner cylinder 34, but with the distal end 38 from the electrodes extending beyond the inner cylinder 34.

In use, the electrode end 32 of the enclosure 30 would be provided with a cover (not shown). Other methods of enclosing the electrode end 32 can be used instead because the means for enclosing the electrode end 32 is not critical to the invention. The distal end 38 of the outer cylinder 36 would be positioned near the area of the patient's skin to be treated, and a blanket or other covering would be placed over the distal end 38 and the part of the patient's body to be treated. A current then would be passed through the bars 10a, 10b to vaporize the bars 10a, 10b and create a mineral rich vapor. The mineral rich vapor would be confined to enclosure 30 and the volume enclosed by the covering and the patient's body. Thus, the vapor will contact the patient's skin and be absorbed. Preferably the mineral rich vapor is applied to the affected area, the upper back, lower back, and the soles of the feet for between approximately 10 and 20 minutes each, preferably approximately 15 minutes each. Preferably the timer 28 limits the treatment to 15 minutes for each part of the body, but this is not critical. Of course, the treatment regimen will vary depending on the individual and the condition being treated.

Preferably the step down transformer 26, timer 28, switch S, and lights L are housed in a power supply assembly 40 is mounted on the enclosure 30. Preferably the bars 10a, 10b, electrodes 22 and 24, power supply assembly 40 and enclosure 30 are mounted on a stand 50 adjustable in height and direction so that the distal end 38 of the outer cylinder 36 can be placed in various positions to treat various portions of various patients.

The heat generated by the burning of the bar 10 will cause the pores in the patient's skin to open, thus facilitating the absorption of the minerals into the body.

Preferably the outer cylinder 36 is adjustably mounted so that the distance between the distal end 38 of the outer cylinder 36 and the bar 10 can be adjusted. Thus, the distance between the vaporizing bar 10 and the skin can be adjusted so that the temperature of the mineral rich vapor when it touches the skin will be comfortable.

Industrial Applicability

This invention is applicable whenever it is desired to administer minerals to a human body in a controlled manner.

What is claimed is:

1. A process for administering essential minerals to a human body through the skin, comprising:

mixing said minerals with graphite and a petrochemical binder to form a bar;

vaporizing said bar, thereby creating a supply of heated vapor containing said minerals;

directing said vapor into contact with said skin, whereby said vapor and said minerals are absorbed through said skin and into said human body.

2. A process according to claim 1, wherein said vaporizing step is carried out by passing an electric current through said bar to cause said bar to burn.

3. A process according to claim 2, wherein said passing step is carried out using a current between approximately 5 amperes and approximately 10 amperes.

4. A process according to claim 3, wherein said current is approximately 7 amperes.

5. A process according to claim 1, wherein said directing step is carried out by directing said vapor into contact successively with the skin on the upper back, the lower back and the bottoms of the feet.

6. A process according to claim 1, wherein said directing step is carried out by directing said vapor into contact with the skin on the upper back for approximately 15 minutes, the skin on the lower back for approximately 15 minutes, and the skin on the bottom of the feet for approximately 15 minutes.

7. A process according to claim 1, wherein said mixing step is carried out using between approximately 70% and approximately 95% by weight graphite, between approximately 1% and approximately 4% by weight petrochemical binder, and between approximately 5% and approximately 20% by weight minerals.

8. A process according to claim 7 wherein said minerals are selected from the group consisting of calcium (Ca), phosphorus (P), sodium (S), potassium (K), chlorine (Cl), magnesium (Mg), sulfur (S), iron (Fe), copper (Cu), zinc (Zn), chromium (Cr), cobalt (Co), manganese (Mn), molybdenum (Mb), vanadium (Vn), selenium (Se), nickel (Ni), tin (Sn), silicon (Si), iodine (I), arsenic (As), aluminum (Al), titanium (Ti), bismuth (Bi), barium (Ba), strontium (Sr), and germanium (Ge).

9. A process according to claim 1, wherein said minerals are selected from the group consisting of zinc, chromium, magnesium, sulfur and selenium.

10. A process for administering minerals to a human body through the skin, comprising:

mixing between approximately 70% and approximately 95% by weight graphite, between approximately 1% and approximately 4% by weight coal tar, between approximately 1% and approximately 3% by weight zinc, between approximately 1% and approximately 3% by weight chromium, between approximately 1% and approximately 3% by weight magnesium, between approximately 1% and 2% by weight sulfur, and between approximately 1% and approximately 3% by weight selenium to form a bar;

applying an electric current of between approximately 5 amperes and approximately 10 amperes to said bar, thereby creating a substantially continuous supply of heated vapor containing minerals; and exposing said skin to said vapor.

* * * * *